United States Patent
Chen et al.

(10) Patent No.: US 10,849,588 B2
(45) Date of Patent: Dec. 1, 2020

(54) METHOD AND APPARATUS FOR DRAWING A CRANIAL IMAGE TRAJECTORY

(71) Applicant: Fussen Technology Co., Ltd., Shenzhen (CN)

(72) Inventors: Minfeng Chen, Shenzhen (CN); Jing Lei, Shenzhen (CN)

(73) Assignee: FUSSEN TECHNOLOGY CO., LTD., Shenzhen (CN)

( * ) Notice: Subject to any disclaimer, the term of this patent is extended or adjusted under 35 U.S.C. 154(b) by 124 days.

(21) Appl. No.: 16/108,038

(22) Filed: Aug. 21, 2018

(65) Prior Publication Data

US 2019/0069867 A1    Mar. 7, 2019

(30) Foreign Application Priority Data

Sep. 1, 2017  (CN) .......................... 2017 1 0781262
Nov. 2, 2017  (CN) .......................... 2017 1 1062542

(51) Int. Cl.
*G06T 7/00*    (2017.01)
*A61B 6/00*    (2006.01)
(Continued)

(52) U.S. Cl.
CPC ............ *A61B 6/5229* (2013.01); *A61B 6/027* (2013.01); *A61B 6/14* (2013.01); *A61B 6/463* (2013.01);
(Continued)

(58) Field of Classification Search
CPC ........... G06T 7/337; G06T 7/344; G06T 3/40; G06T 2207/10116; G06T 2207/30008;
(Continued)

(56) References Cited

U.S. PATENT DOCUMENTS 6,600,831 B1 * 7/2003 Sasada ...................... G06T 7/30
                                                    382/132
6,766,058 B1 * 7/2004 Wilson ................. G06K 9/4609
                                                    348/130

(Continued)

FOREIGN PATENT DOCUMENTS

CN        107004269 A      8/2017
CN        107273657 A      10/2017

OTHER PUBLICATIONS

Hutton et al "An evaluation of active shape models for the automatic identification of cephalometric landmarks" European Orthodontic Society 2000.*

(Continued)

*Primary Examiner* — Sean T Motsinger
(74) *Attorney, Agent, or Firm* — Hemisphere Law, PLLC; Zhigang Ma

(57) ABSTRACT

The present disclosure discloses a method for drawing a cranial image trajectory. The method comprises: providing, by a processor, at least one trajectory pattern template for parts of a standard cranial anatomy; acquiring, by a radiation image device, at least one cranial image of a patient, superimposing, by the processor, the trajectory pattern template of each part of the standard cranial anatomy onto the corresponding position of the patient's cranial image, and acquiring the trajectory pattern of the cranial image; and if a deviation is determined between the shape of the respective structure on the trajectory pattern of the patient's cranial image and that of the trajectory pattern template of each part of the standard cranial anatomy, adjusting the shape of the corresponding trajectory pattern template in the cranial anatomy so as to be the same as the respective structure in the cranial image by the processor.

13 Claims, 4 Drawing Sheets

(51) Int. Cl.
 *G06T 7/33* (2017.01)
 *A61B 6/02* (2006.01)
 *A61B 6/14* (2006.01)
 *G06T 3/40* (2006.01)

(52) U.S. Cl.
 CPC .............. *A61B 6/488* (2013.01); *A61B 6/501* (2013.01); *G06T 3/40* (2013.01); *G06T 7/337* (2017.01); *G06T 7/344* (2017.01); *G06T 2207/10116* (2013.01); *G06T 2207/30008* (2013.01); *G06T 2207/30016* (2013.01); *G06T 2207/30241* (2013.01)

(58) Field of Classification Search
 CPC . G06T 2207/30016; G06T 2207/30241; A61B 6/027; A61B 6/14; A61B 6/463; A61B 6/488; A61B 6/501; A61B 6/5229
 See application file for complete search history.

(56) References Cited

U.S. PATENT DOCUMENTS

| | | | | |
|---|---|---|---|---|
| 9,125,709 | B2 * | 9/2015 | Matty | A61C 7/002 |
| 2003/0109784 | A1 * | 6/2003 | Loh | B29C 64/153 |
| | | | | 600/427 |
| 2004/0029068 | A1 * | 2/2004 | Sachdeva | G16H 50/50 |
| | | | | 433/24 |
| 2005/0010868 | A1 * | 1/2005 | Schowtka | G06T 3/40 |
| | | | | 715/253 |
| 2006/0094951 | A1 * | 5/2006 | Dean | A61F 2/30942 |
| | | | | 600/407 |
| 2006/0246450 | A1 * | 11/2006 | Franch | C07H 21/04 |
| | | | | 435/6.12 |
| 2007/0072144 | A1 * | 3/2007 | Imgrund | A61C 7/00 |
| | | | | 433/24 |
| 2009/0003667 | A1 * | 1/2009 | Cheng | G06K 9/4604 |
| | | | | 382/128 |
| 2010/0167243 | A1 * | 7/2010 | Spiridonov | A61C 7/00 |
| | | | | 433/224 |
| 2012/0223970 | A1 * | 9/2012 | Cortes Provencio | A61B 5/1079 |
| | | | | 345/646 |
| 2015/0342545 | A1 * | 12/2015 | Bergersen | A61B 6/14 |
| | | | | 378/62 |
| 2016/0239631 | A1 * | 8/2016 | Wu | A61C 7/002 |
| 2016/0275679 | A1 * | 9/2016 | Im | A61B 6/032 |
| 2017/0189717 | A1 * | 7/2017 | MacDonald | A61B 6/037 |
| 2017/0337680 | A1 | 11/2017 | Weber et al. | |
| 2019/0069867 | A1 * | 3/2019 | Chen | G06T 7/337 |
| 2019/0102884 | A1 * | 4/2019 | Hsin | G16H 50/50 |

OTHER PUBLICATIONS

El-Feghi "Automatic Localization of craniofacial landmarks for assisted cephalometry" Pattern Recognition 2004.*

* cited by examiner

METHOD AND APPARATUS FOR DRAWING A CRANIAL IMAGE TRAJECTORY

TECHNICAL FIELD

The disclosure relates to the field of orthodontics, in particular to an apparatus and a method for drawing a cranial image trajectory.

BACKGROUND

X-ray cephalometric analysis technology is often used to analyze X-ray cranial images to identify special anatomical points on the teeth, jaw, cranial, and face. The craniomaxillofacial morphology is described by the line spacing, line spacing ratio, and angle determined by the X-ray cephalometric analysis technology, so as to help doctors determine the structures of the dental and soft or hard tissues on the surface of the calvarium, and provide scientific basis for the orthodontic diagnosis and treatment plan of patients. Therefore, X-ray cephalometric analysis technology is important for clinical diagnosis, treatment plan and research work of orthodontic and oral surgery, etc.

The cephalometric trajectories are the results of drawing accurate trajectory pattern for individual tissue structures in the X-ray cranial image. There are many types of software that generate trajectory patterns on the market, with different functions and different principles. Popular methods are curve fitting method and stream input method. Curve fitting needs to input a large number of consecutive points, which needs to be drawn on a sulfuric acid paper, and the procedure is complicated. The stream input method is to record the path taken by the mouse in a short time interval so as to connect them into a line. Curve fitting needs to input a large number of points, with the risk of repeated depiction.

SUMMARY

One of the purposes of the present disclosure is to provide an apparatus and a method for drawing a cranial image trajectory, to quickly generate a cranial image trajectory, have a simple operation, and avoid the risk of repeated depiction, and may accurately locate an orthodontic position for a patient.

The purpose of the present disclosure may be achieved by adopting the following technical measures to design a method for drawing a cranial image trajectory. The steps of the method include: providing at least one trajectory pattern template for parts of a standard cranial anatomy; acquiring a cranial image of a patient, superimposing the trajectory pattern template of each part of the standard cranial anatomy onto the corresponding position of the patient's cranial image, and acquiring the trajectory pattern of the cranial image; and if a deviation is determined between the shape of the respective structure on the trajectory pattern of the patient's cranial image and that of the trajectory pattern template of each part of the standard cranial anatomy, adjusting the shape of the corresponding trajectory pattern template in the cranial anatomy so as to be the same as the respective structure in the cranial image.

The purpose of the present disclosure may be achieved by adopting the following technical measures to design an apparatus drawing a cranial image trajectory, comprising a processor and a computer-readable storage medium, wherein the processor acquires a computer program on the computer-readable storage medium and executes: providing at least one trajectory pattern template for parts of a standard cranial anatomy; acquiring a cranial image of a patient, superimposing the trajectory pattern template of each part of the standard cranial anatomy onto the corresponding position of the patient's cranial image, and acquiring the trajectory pattern of the cranial image; and if a deviation is determined between the shape of the respective structure on the trajectory pattern of the patient's cranial image and that of the trajectory pattern template of each part of the standard cranial anatomy, adjusting the shape of the corresponding trajectory pattern template in the cranial anatomy so as to be the same as the respective structure in the cranial image.

Different from the prior art, the present method may quickly generate a cranial image trajectory, have a simple operation, and avoid the risk of repeated depiction, and may accurately locate an orthodontic position for the patient.

DETAILED DESCRIPTION

The technical solutions of the present disclosure will be further described in detail below in conjunction with specific embodiments. Obviously, the described embodiments are merely a part of the embodiments of the present disclosure, rather than all the embodiments. All other embodiments obtained by a person of ordinary skill in the art based on the embodiments of the present disclosure without creative efforts shall fall within the protection scope of the present disclosure.

Figure 1:
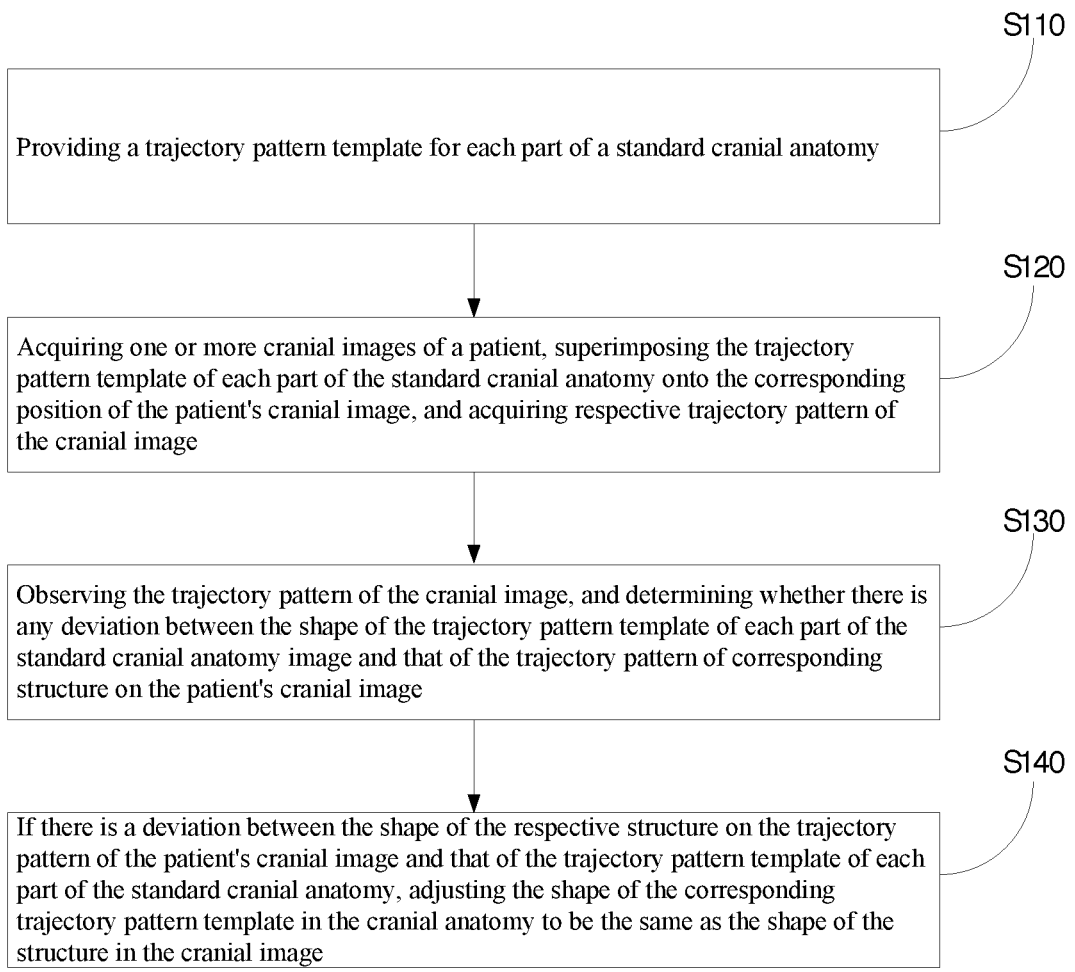
FIG. 1 is a schematic flowchart of a method for drawing a cranial image trajectory, according to one embodiment of the present disclosure.

Referring to FIG. 1, which is a schematic flowchart of a method for drawing a cranial image trajectory provided by the present disclosure. In the actual treatment, especially in the orthodontic treatment process, the patients are usually photographed with X-rays and the patient's X-ray photographs/images are taken to illustrate the pathology. However, it is hard for a non-specialized patient to understand the X-rays images since the images are abstract, causing inconvenience to the doctor's treatment. The present disclosure provides a method for distinguishing different structures through lines in a patient's X-ray image to obtain a trajectory of the X-ray cranial image. As such, the doctors may detect the shape of each structure in the patient's cranial image through the trajectory, to determine whether lesions occur, and determine a treatment plan. The present disclosure is implemented based on a computer and a similar image processing system. In this embodiment, the present disclosure uses a computer to illustrate. The steps of this method include:

S110: Providing a trajectory pattern template for each part of a standard cranial anatomy.

Figure 2:
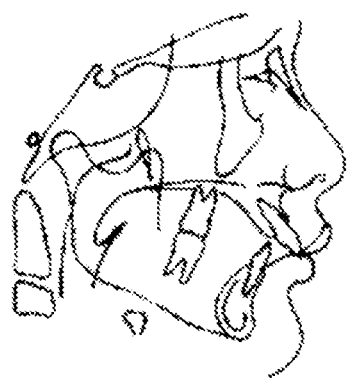
FIG. 2 shows a trajectory pattern template for parts of a standard cranial anatomy by using the method for drawing a cranial image trajectory.

In the present disclosure, a trajectory pattern of a standard cranial structure is first provided. When selecting the trajectory patterns, it should be selected according to the actual situation of the patient, e.g. the patient's gender, age, weight, and cranial features. Therefore, trajectory patterns for different patients should be different. However, the trajectory pattern is at least required to be a complete structure, and images corresponding to structures in different parts should be identified, as shown in FIG. 2. After being acquired, the trajectory pattern for the standard cranial structure is decomposed, to obtain multiple trajectory patterns for the decomposed structures of the standard cranium, as the desired trajectory pattern templates of the present disclosure. In the present embodiment, the process of decomposing the trajectory pattern for standard cranial structure is performed by drawing software installed in a computer. After the decomposition is completed, each trajectory pattern template for respective anatomical structure is saved in a picture format, e.g. MPEG, or the trajectory pattern templates are stored in another suitable format on computer. In the present embodiment, after the standard cranial structure image is decomposed, trajectory pattern template for each anatomy structure of the palate portion, upper middle incisor teeth, lower middle incisor teeth, mandibular bone, first upper molar, first lower molar, pterygomaxillary fissure, orbital edge, nasal bone, facial contour, pituitary fossa, ear contour, frontal orbital surface, and ala major ossis sphenoidalis (cerebral surface) is obtained. The trajectory patterns for the above structures may be combined to form a complete cranial structure trajectory pattern. At the same time, in other embodiments, the standard cranial structure may also be decomposed according to other decomposition criteria.

S120: Acquiring one or more cranial images of a patient, superimposing the trajectory pattern template of each part of the standard cranial anatomy onto the corresponding position of the patient's cranial image, and acquiring respective trajectory pattern of the cranial image.

After decomposing the standard cranial structure to obtain the trajectory pattern template of each part of the anatomy structure, the cranial image of the currently treated patient is extracted. The cranial image is stored in a storage apparatus and needs to be displayed by a display apparatus. The patient's cranial image is an X-ray kind image, or other kind of image which is used for orthodontics. Preferably, the cranial image includes the images captured in left side, right side, and front, respectively. In the present embodiment, an example of the patient cranial image captured by X-ray will be described. After acquiring the cranial image of the patient, the X-ray image(s) is/are displayed on the computer. Preferably, it may be displayed by using drawing software such as Photoshop, or other similar drawing software. After displaying the above three different aspects of the patient's cranial image on the computer, the trajectory pattern template(s) obtained in step S110 is sequentially superimposed on the corresponding position of the patient's cranial image. In the present disclosure, the trajectory pattern template shows the outline edge of the corresponding structure, and represents the outline/contour of the standard, non-lesioned or healthy structure. However, the acquired cranial image of the patient is an X-ray image, and the distinction between adjacent structures is not obvious, and patients often cannot recognize the respective structure in the image therein. Therefore, it is very difficult for a patient to judge whether a treatment is needed or not, which may cause distrust from the patient. To solve such problem, the trajectory pattern template obtained in step of S110 is superimposed onto the X-ray image captured in this step, and the corresponding trajectory pattern template for respective structure is superimposed to the corresponding structure on the X-ray image, as such, a trajectory pattern of the cranial image is obtained.

In this embodiment, the cranial images of the patient are captured by X-ray camera which is coupled to the computer which implements the method. It is understood that the cranial images can be captured by other kinds of radiation image device. In addition, the cranial images can also be acquired by transmission from other storage device, and not limited to any of the implementations mentioned above.

S130: Detecting the trajectory pattern of the cranial image, and determining whether there is any deviation between the shape of the trajectory pattern template of each part of the standard cranial anatomy image and that of the trajectory pattern of corresponding structure on the patient's cranial image.

In the present disclosure, the trajectory pattern of the cranial image obtained in step S120 can be observed or detected, to see if the structures in the trajectory of the cranial image match the trajectory template. That is, it is determined whether the line profile in the trajectory pattern template coincides with the edge of each structure in the trajectory of the cranial image. If they are coincident, it indicates that the patient's structure is substantially the same as the corresponding structure in the standard cranium structure, thus it is diagnosed the present structure is normal and not necessary to have treatment or orthodontics. On the other hand, if they are not coincident, it is indicates that the cranial structure of the patient and the corresponding structure of the normal/standard cranial image are not match and needed to be corrected.

S140: If there is a deviation between the shape of the respective structure on the trajectory pattern of the patient's cranial image and that of the trajectory pattern template of each part of the standard cranial anatomy, adjusting the shape of the corresponding trajectory pattern template in the cranial anatomy to be the same as the shape of the structure in the cranial image.

Specifically, if the shape profile of the structure in the cranial image of the patient detected in the previous step is different from that of the standard cranial structure, the lines of the trajectory pattern template superimposed to the patient's cranial image should be adjusted after a corresponding record is made. For example, by the way of zooming in, zooming out, adjusting the angle, and adjusting the line trajectory of the trajectory pattern template, etc., the trajectory pattern template can be adjusted to have the same trajectory as the corresponding structure in the patient's cranial image. After the adjustment is complete, a trajectory pattern of the patient's cranial image is obtained. When explaining the patient's condition, the doctor compares the difference between the trajectory pattern of the patient's cranial image and the standard cranial anatomy, so as the patient believes that the deviated structure(s) in the cranial image is/are the structures that need to be corrected or treated.

In other embodiments of the present disclosure, the trajectory pattern templates for the respective structure may be superimposed on the patient's cranial image one by one, and then detect and adjust the templates to ensure the structure contour of the corresponding structure in the superimposed trajectory template is the same to the patient's cranial image. After that, choose other trajectory templates corresponding to other structures to superimpose into the patient's cranial image.

Different from the prior art, the method for drawing a cranial image trajectory in the present disclosure comprises the steps of: providing at least one trajectory pattern template for parts of a standard cranial anatomy; acquiring at least one cranial image of a patient, superimposing the trajectory pattern template of each part of the standard cranial anatomy onto the corresponding position of the patient's cranial image, and acquiring the trajectory pattern of the cranial image; and if a deviation is determined, between the shape of the respective structure on the trajectory pattern of the patient's cranial image and that of the trajectory pattern template of each part of the standard cranial anatomy, adjusting the shape of the corresponding trajectory pattern template in the cranial anatomy so as to be the same as the respective structure in the cranial image. By using this method, a cranial image trajectory pattern may be quickly generated, with simple operation, and the risk of repetitive drawing is avoided, and the orthodontic position of the patient may be accurately determined.

Figure 3:
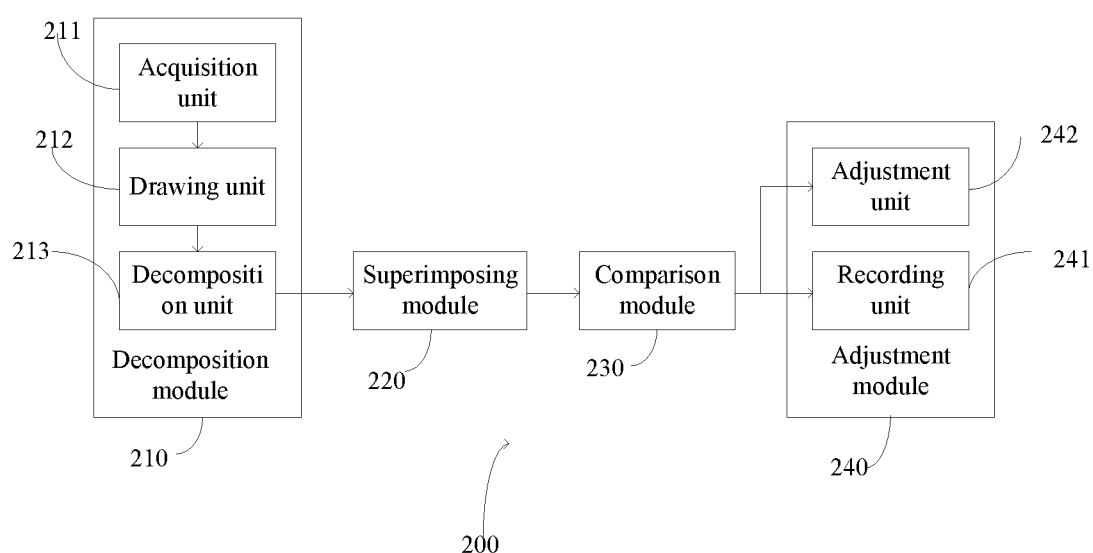
FIG. 3 is a schematic block diagram of an apparatus for drawing a cranial image trajectory, according to another embodiment of the present disclosure.

Referring to FIG. 3, FIG. 3 is a schematic block diagram of an apparatus for drawing a trajectory pattern of a cranial image provided by the present disclosure. The apparatus 200 includes a decomposition module 210, a superimposing module 220, a comparison module 230, and an adjustment module 240.

Wherein, the decomposition module 210 is configured to decompose the standard cranial anatomy and obtain the trajectory pattern templates of respective parts of the standard cranial anatomy.

In the present disclosure, a trajectory pattern of a standard cranial structure is first provided. When selecting the trajectory patterns, it should be selected according to the actual situation of the patient, e.g. the patient's gender, age, weight, and cranial features. Therefore, trajectory patterns for different patients should be different. However, the trajectory pattern is at least required to be a complete structure, and images corresponding to structures in different parts should be identified, as shown in FIG. 2. After being acquired, the trajectory pattern for the standard cranial structure is decomposed by the decomposition module 210, to obtain multiple trajectory patterns for the decomposed structures of the standard cranium, as the desired trajectory pattern templates of the present disclosure. The decomposition module 210 includes an acquisition unit 211, a drawing unit 212, and a decomposition unit 213. In the present embodiment, the acquisition unit 211 is configured to acquire image for standard cranium, the drawing unit 212 is configured to draw a standard trajectory pattern for the standard cranial image, and the decomposition unit 213 is configured to decompose the standard cranial image, and the process of decomposing the trajectory pattern for standard cranial structure is performed by drawing software installed in a computer. After the decomposition is completed, each trajectory pattern template for respective anatomical structure is saved in a picture format, e.g. MPEG, or the trajectory pattern templates are stored in another suitable format on computer. In the present embodiment, after the standard cranial structure image is decomposed, trajectory pattern template for each anatomy structure of the palate portion, upper middle incisor teeth, lower middle incisor teeth, mandibular bone, first upper molar, first lower molar, pterygomaxillary fissure, orbital edge, nasal bone, facial contour, pituitary fossa, ear contour, frontal orbital surface, and ala major ossis sphenoidalis (cerebral surface) is obtained. The trajectory patterns for the above structures may be combined to form a complete cranial structure trajectory pattern. At the same time, in other embodiments, the standard cranial structure may also be decomposed by the decomposition module 210 according to other decomposition criteria.

The superimposing module 220 is configured to acquire one or more cranial images of a patient, superimpose the trajectory pattern template of each part of the standard cranial anatomy onto the corresponding position of the patient's cranial image, and acquire respective trajectory pattern of the cranial image.

After decomposing the standard cranial structure to obtain the trajectory pattern template of each part of the anatomy structure, the cranial image of the currently treated patient is extracted. The cranial image is stored in a storage apparatus and needs to be displayed by a display apparatus. The patient's cranial image is an X-ray kind image, or other kind of image which is used for orthodontics. Preferably, the cranial image includes the images captured in left side, right side, and front, respectively. In the present embodiment, an example of the patient cranial image captured by X-ray will be described. After acquiring the cranial image of the patient, the X-ray image(s) is/are displayed on the computer. Preferably, it may be displayed by using drawing software such as Photoshop, or other similar drawing software. After displaying the above three different aspects of the patient's cranial image on the computer, the superimposing module 220 sequentially superimpose the trajectory pattern template(s) on the corresponding position of the patient's cranial image. In the present disclosure, the trajectory pattern template shows the outline edge of the corresponding structure, and represents the outline/contour of the standard, non-lesioned or healthy structure. However, the acquired cranial image of the patient is an X-ray image, and the distinction between adjacent structures is not obvious, and patients often cannot recognize the respective structure in the image therein. Therefore, it is very difficult for a patient to judge whether a treatment is needed or not, which may cause distrust from the patient. To solve such problem, the trajectory pattern template obtained in step of S110 is superimposed onto the X-ray image captured in this step, and the corresponding trajectory pattern template for respective structure is superimposed to the corresponding structure on the X-ray image, as such, a trajectory pattern of the cranial image is obtained.

The comparison module 230 is configured to detect the trajectory pattern of the cranial image, and determine whether there is any deviation between the shape of the trajectory pattern template of each part of the standard cranial anatomy image and that of the trajectory pattern of corresponding structure on the patient's cranial image.

The comparison module 230 compares the trajectory pattern of the cranial image to the trajectory image, to see if the structures in the trajectory of the cranial image match the trajectory template. That is, it is capable of determining whether the line profile in the trajectory pattern template coincides with the edge of each structure in the trajectory of the cranial image. If they are coincident, it indicates that the patient's structure is substantially the same as the corresponding structure in the standard cranium structure, thus it is diagnosed the present structure is normal and not necessary to have treatment or orthodontics. On the other hand, if they are not coincident, it is indicates that the cranial structure of the patient and the corresponding structure of the normal/standard cranial image are not match and needed to be corrected.

The adjustment module 240 is configured to adjust the shape of the corresponding trajectory pattern template in the cranial anatomy, when there is a deviation between the shape of the respective structure on the trajectory pattern of the patient's cranial image and that of the trajectory pattern template of each part of the standard cranial anatomy, so as the shape of the corresponding trajectory pattern template in the cranial anatomy to be the same as the shape of the structure in the cranial image.

The adjustment module 240 includes a recording unit 241 and an adjustment unit 242. The recording unit 241 records all of the structure trajectory in the cranial anatomy trajectory template and the structure trajectory in the patient cranial image which is corresponding to the trajectory template; the adjustment unit 242 adjusts the lines of the trajectory template through curve adjustment, to adjust the trajectory.

If the shape profile of the structure in the cranial image of the patient detected in the previous step is different from that of the standard cranial structure, the lines of the trajectory pattern template superimposed to the patient's cranial image should be adjusted after a corresponding record is made by the recording unit 241. For example, through the adjustment unit 232, by the way of zooming in, zooming out, adjusting the angle, and adjusting the line trajectory of the trajectory pattern template, etc., the trajectory pattern template can be adjusted to have the same trajectory as the corresponding structure in the patient's cranial image. After the adjustment is complete, a trajectory pattern of the patient's cranial image is obtained. When explaining the patient's condition, the doctor compares the difference between the trajectory pattern of the patient's cranial image and the standard cranial anatomy, so as the patient believes that the deviated structure(s) in the cranial image is/are the structures that need to be corrected or treated.

In other embodiments of the present disclosure, the trajectory pattern templates for the respective structure may be superimposed on the patient's cranial image one by one, and then detect and adjust the templates to ensure the structure contour of the corresponding structure in the superimposed trajectory template is the same to the patient's cranial image. After that, choose other trajectory templates corresponding to other structures to superimpose into the patient's cranial image.

Different from the prior art, the method for drawing a cranial image trajectory in the present disclosure comprises: a decomposition module 210 is configured to decompose the standard cranial anatomy and obtain the trajectory pattern templates of respective parts of the standard cranial anatomy. The superimposing module 220 is configured to acquire one or more cranial images of a patient, superimpose the trajectory pattern template of each part of the standard cranial anatomy onto the corresponding position of the patient's cranial image, and acquire respective trajectory pattern of the cranial image. The comparison module 230 is configured to detect the trajectory pattern of the cranial image, and determine whether there is any deviation between the shape of the trajectory pattern template of each part of the standard cranial anatomy image and that of the trajectory pattern of corresponding structure on the patient's cranial image. The adjustment module 240 is configured to adjust the shape of the corresponding trajectory pattern template in the cranial anatomy, when there is a deviation between the shape of the respective structure on the trajectory pattern of the patient's cranial image and that of the trajectory pattern template of each part of the standard cranial anatomy, so as the shape of the corresponding trajectory pattern template in the cranial anatomy to be the same as the shape of the structure in the cranial image. By using this apparatus, a cranial image trajectory pattern may be quickly generated, with simple operation, and the risk of repetitive drawing is avoided, and the orthodontic position of the patient may be accurately determined.

Figure 4:
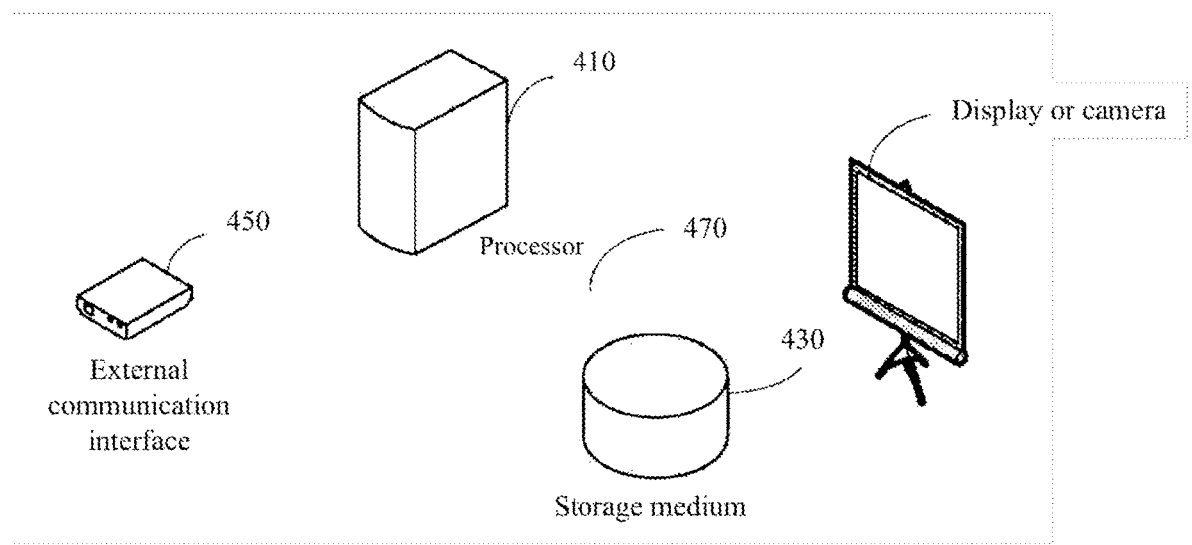
FIG. 4 shows an apparatus for drawing a cranial image trajectory according to an exemplary embodiment.

As shown in FIG. 4, the present example provides an apparatus for drawing a cranial image trajectory, including a processor 410, a storage medium 430 and at least one external communications interfaces 450. The processor 410, the storage medium 430 and the at least one external communications interfaces 450 are all connected by using a bus 470. The processor 410 may be an electronic component having a processing function, for example, a microprocessor, a central processing unit, a digital signal processor, an application processor or a programmable logic array. The store medium 430 stores computer executable instructions. The processor 410 executes the computer executable instructions stored in the store medium 430, and may implement the method for drawing a cranial image trajectory provided by any technical solution of the foregoing embodiments, for example, the method as shown in FIG. 1.

In the several embodiments provided in this application, it should be understood that the disclosed device and method may be implemented in other manners. The described device embodiments are merely exemplary. For example, the unit division is merely logical function division and may be other division during actual implementation. For example, multiple units or components may be combined or integrated into another system, or some features may be ignored or not performed. In addition, the displayed or discussed mutual couplings or direct couplings or communication connections between the components may be implemented through some interfaces, indirect couplings or communication connections between the devices or units, or electrical connections, mechanical connections, or connections in other forms.

The units described as separation parts may be or may not be physically separated. The part used as display unit may be or may not be a physical unit. That is, the units may be located in a same place, or may be distributed to many network units. Some or all of the units may be selected according to actual requirements to implement the purpose of the solution of the exemplary embodiments.

In addition, functional units in one or more exemplary embodiments may be all integrated in a processing module, each unit is separately used as a unit, or two or more units are integrated in a unit. The integrated unit may be implemented in a form of hardware, or may be implemented in form of hardware plus a software functional unit.

A person of ordinary skill in the art may understand that, some or all of steps for implementing the method embodiments may be implemented by using hardware related to a program instruction. The program may be stored in a computer readable storage medium such as non-transitory computer-readable medium. When the program is executed, the steps including the method embodiments are performed. However, the storage medium includes various types of media that may store program code, for example, a mobile storage device, a read-only memory (ROM), a random access memory (RAM), a magnetic disk, or an optical disk.

The foregoing descriptions are merely specific implementations of the present disclosure, but are not intended to limit the protection scope of the present disclosure. Any variation or replacement readily figured out by a person skilled in the art within the technical scope disclosed in the present disclosure shall fall within the protection scope of the present disclosure. Therefore, the protection scope of the present disclosure shall be subject to the protection scope of the claims.

What is claimed is:

1. A method for drawing a cranial image trajectory, comprising:
providing, by a processor, at least one trajectory pattern template for parts of a standard cranial anatomy, wherein a trajectory pattern for a standard cranial structure is decomposed, to obtain multiple trajectory patterns for the decomposed structures of the standard cranium, as the at least one trajectory pattern template;

acquiring, by a radiation image device, at least one cranial image of a patient, superimposing, by the processor, the trajectory pattern template of each part of the standard cranial anatomy onto the corresponding position of the patient's cranial image one by one, and acquiring a first trajectory pattern of the cranial image; and if a deviation is determined between the shape of the respective structure on the first trajectory pattern of the patient's cranial image and that of the trajectory pattern template of each part of the standard cranial anatomy, adjusting the shape of the corresponding trajectory pattern template in the cranial anatomy so as to be the same as the respective structure of the first trajectory pattern in the cranial image by the processor; and obtaining a second trajectory pattern of the patient's cranial image after the adjustment is complete.

2. The method according to claim 1, wherein providing at least one trajectory pattern template for parts of a standard cranial anatomy, comprises:

acquiring at least one standard cranial image;

drawing a standard cranial image trajectory according to the standard cranial image;

anatomically decomposing the standard cranial image trajectory to obtain respective trajectory pattern template for each part of the standard cranial anatomy.

3. The method according to claim 1, wherein adjusting the shape of the corresponding trajectory pattern template in the cranial anatomy so as to be the same as the respective structure in the cranial image, comprises:

recording the corresponding structure of the cranial anatomy trajectory template and that in the cranial image of the patient;

adjusting the trajectory of the trajectory pattern template.

4. The method according to claim 3, wherein the way of adjusting the trajectory of the trajectory pattern template comprises: zooming in.

5. The method according to claim 3, wherein the way of adjusting the trajectory of the trajectory pattern template comprises: zooming out.

6. The method according to claim 3, wherein the way of adjusting the trajectory of the trajectory pattern template comprises: adjusting the angle of the trajectory pattern template.

7. The method according to claim 3, wherein the way of adjusting the trajectory of the trajectory pattern template comprises: adjusting the lines of the trajectory.

8. An apparatus for drawing a cranial image trajectory, comprising a processor and a computer-readable storage medium, wherein the processor acquires a computer program on the computer-readable storage medium and executes:

providing at least one trajectory pattern template for parts of a standard cranial anatomy, wherein a trajectory pattern for a standard cranial structure is decomposed, to obtain multiple trajectory patterns for the decomposed structures of the standard cranium, as the at least one trajectory pattern template;

acquiring a cranial image of a patient;

superimposing the trajectory pattern template of each part of the standard cranial anatomy onto the corresponding position of the patient's cranial image one by one, and acquiring a first trajectory pattern of the cranial image; and if a deviation is determined, between the shape of the respective structure on the first trajectory pattern of the patient's cranial image and that of the trajectory pattern template of each part of the standard cranial anatomy, adjusting the shape of the corresponding trajectory pattern template in the cranial anatomy so as to be the same as the respective structure of the first trajectory pattern in the cranial image; and obtaining a second trajectory pattern of the patient's cranial image after the adjustment is complete.

9. The apparatus according to claim 8, wherein providing at least one trajectory pattern template for parts of a standard cranial anatomy comprises:

acquiring at least one standard cranial image;

drawing a standard cranial image trajectory according to the standard cranial image;

anatomically decomposing the standard cranial image trajectory to obtain respective trajectory pattern template for each part of the standard cranial anatomy.

10. The apparatus according to claim 8, wherein adjusting the shape of the corresponding trajectory pattern template in the cranial anatomy so as to be the same as the respective structure in the cranial image comprises:

recording the corresponding structure of the cranial anatomy trajectory template and that in the cranial image of the patient;

adjusting the trajectory of the trajectory pattern template.

11. A non-transitory computer-readable medium storing computerized code that when executed by an electronic apparatus comprising memory and one or more processors, causes the processor to:

provide at least one trajectory pattern template for parts of a standard cranial anatomy, wherein a trajectory pattern for a standard cranial structure is decomposed, to obtain multiple trajectory patterns for the decomposed structures of the standard cranium, as the at least one trajectory pattern template;

acquire a cranial image of a patient, superimpose the trajectory pattern template of each part of the standard cranial anatomy onto the corresponding position of the patient's cranial image one by one, and obtain a first trajectory pattern of the cranial image; and if a deviation is determined, between the shape of the respective structure on the first trajectory pattern of the patient's cranial image and that of the trajectory pattern template of each part of the standard cranial anatomy, adjust the shape of the corresponding trajectory pattern template in the cranial anatomy so as to be the same as the respective structure of the first trajectory pattern in the cranial image; and obtain a second trajectory pattern of the patient's cranial image after the adjustment is complete.

12. The non-transitory computer-readable medium according to claim 11, wherein providing at least one trajectory pattern template for parts of a standard cranial anatomy comprises:

acquiring at least one standard cranial image;

drawing a standard cranial image trajectory according to the standard cranial image;

anatomically decomposing the standard cranial image trajectory to obtain respective trajectory pattern template for each part of the standard cranial anatomy.

13. The non-transitory computer-readable medium according to claim 11, wherein adjusting the shape of the corresponding trajectory pattern template in the cranial anatomy so as to be the same as the respective structure in the cranial image comprises:

recording the corresponding structure of the cranial anatomy trajectory template and that in the cranial image of the patient;

adjusting the trajectory of the trajectory pattern template.

* * * * *